(12) United States Patent
Liu et al.

(10) Patent No.: US 10,584,359 B2
(45) Date of Patent: Mar. 10, 2020

(54) **GENETICALLY RECOMBINANT *SACCHAROMYCES CEREVISIAE* FOR DEGRADING KITCHEN WASTE**

(71) Applicant: Guangdong Recyclean Low-Carbon Technology, Guangzhou, Guangdong (CN)

(72) Inventors: Zehuan Liu, Guangdong (CN); Long Fang, Guangdong (CN); Kai Yan, Guangdong (CN); Xiaolong Kang, Guangdong (CN); Yangyang Zheng, Guangdong (CN); Renhuai Liu, Guangdong (CN); Jianghai Lin, Guangdong (CN); Wenjuan Xiao, Guangdong (CN); Jingbo Li, Guangdong (CN); Yingxue Gong, Guangdong (CN)

(73) Assignee: Guangdong Recyclean Low-Carbon Technology, Guangzhou, Guangdong (CN)

( * ) Notice: Subject to any disclaimer, the term of this patent is extended or adjusted under 35 U.S.C. 154(b) by 95 days.

(21) Appl. No.: 15/109,018

(22) PCT Filed: Mar. 21, 2014

(86) PCT No.: PCT/CN2014/073890
§ 371 (c)(1),
(2) Date: Jun. 29, 2016

(87) PCT Pub. No.: WO2015/100856
PCT Pub. Date: Jul. 9, 2015

(65) Prior Publication Data
US 2017/0226539 A1  Aug. 10, 2017

(30) Foreign Application Priority Data
Dec. 30, 2013 (CN) .......................... 2013 1 0742190

(51) Int. Cl.
| | | |
|---|---|---|
| *C12N 9/48* | (2006.01) | |
| *C12P 7/08* | (2006.01) | |
| *C12N 9/34* | (2006.01) | |
| *C12N 9/26* | (2006.01) | |
| *C12N 1/16* | (2006.01) | |
| *C12N 9/28* | (2006.01) | |

(52) U.S. Cl.
CPC .................. *C12P 7/08* (2013.01); *C12N 1/16* (2013.01); *C12N 9/2414* (2013.01); *C12N 9/2417* (2013.01); *C12N 9/2428* (2013.01); *C12N 9/48* (2013.01); *C12Y 302/01001* (2013.01); *C12Y 302/01003* (2013.01)

(58) Field of Classification Search
None
See application file for complete search history.

(56) References Cited

U.S. PATENT DOCUMENTS

| | | | |
|---|---|---|---|
| 5,231,017 A | 7/1993 | Lantero et al. | |
| 8,048,657 B2 * | 11/2011 | Breneman | C12N 9/242 435/162 |

FOREIGN PATENT DOCUMENTS

| | | |
|---|---|---|
| CN | 1831110 A | 9/2006 |
| CN | 101319225 A | 12/2008 |
| CN | 101717795 A | 6/2010 |
| JP | 2003-240 A | 1/2003 |

OTHER PUBLICATIONS

Yamasita et al., Agricultural and Biological Chemistry, 1986, vol. 50:1, pp. 109-113.*
de Morases et al., Appl Microbiol Biotechnol, 1995, vol. 43, pp. 1067-1076.*
Ze-huan et al., Nov 2012, Journal of Shenzhen University Science and Engineering, vol. 29(6), pp. 548-552.*

* cited by examiner

*Primary Examiner* — Mindy G Brown
(74) *Attorney, Agent, or Firm* — Muncy, Geissler, Olds & Lowe, P.C.

(57) ABSTRACT

Disclosed is a genetically recombinant *Saccharomyces cerevisiae* useful for degrading and utilizing kitchen wastes. Genes encoding α-amylase (AMY), glucoamylase (GA) and acid protease (AP) were introduced into the genetically recombinant *Saccharomyces cerevisiae* using a *Saccharomyces cerevisiae* multi-gene co-expression vector and successfully expressed and secreted. The *Saccharomyces cerevisiae* so obtained are capable of secreting amylases and protease to degrade the starch and proteins in kitchen wastes to produce carbon and nitrogen sources such as glucose, polypeptides and amino acids, allowing fermentation into ethanol.

10 Claims, 3 Drawing Sheets
Specification includes a Sequence Listing.

SEQUENCE LISTING

<160> NUMBER OF SEQ ID NOS: 9

<210> SEQ ID NO 1
<211> LENGTH: 1500
<212> TYPE: DNA
<213> ORGANISM: Aspergillus oryzae

<400> SEQUENCE: 1

```
atgatggtcg cgtggtggtc tctatttctg tacggccttc aggtcgcggc acctgctttg      60
gctgcaacgc ctgcggactg gcgatcgcaa tccatttatt tccttctcac ggatcgattt     120
gcaaggacgg atgggtcgac gactgcgact tgtaatactg cggatcagaa atactgtggt     180
ggaacatggc agggcatcat cgacaagttg gactatatcc agggaatggg cttcacagcc     240
atctggatca cccccgttac agcccagctg ccccagacca ccgcatatgg agatgcctac     300
catggctact ggcagcagga tatatactct ctgaacgaaa actacggcac tgcagatgac     360
ttgaaggcgc tctcttcggc ccttcatgag aggggggatgt atcttatggt cgatgtggtt     420
gctaaccata tgggctatga tggagcgggt agctcagtcg attacagtgt gtttaaaccg     480
ttcagttccc aagactactt ccacccgttc tgtttcattc aaaactatga agatcagact     540
caggttgagg attgctggct aggagataac actgtctcct tgcctgatct cgataccacc     600
aaggatgtgg tcaagaatga atggtacgac tgggtgggat cattggtatc gaactactcc     660
attgacggcc tccgtatcga cacagtaaaa cacgtccaga aggacttctg gcccgggtac     720
aacaaagccg caggcgtgta ctgtatcggc gaggtgctcg acggtgatcc ggcctacact     780
tgtccctacc agaacgtcat ggacggcgta ctgaactatc ccatttacta tccactcctc     840
aacgccttca agtcaacctc cggcagcatg gacgacctct acaacatgat caacaccgtc     900
aaatccgact gtccagactc aacactcctg ggcacattcg tcgagaacca cgacaaccca     960
cggttcgctt cttacaccaa cgacatagcc ctcgccaaga acgtcgcagc attcatcatc    1020
ctcaacgacg gaatccccat catctacgcc ggccaagaac agcactacgc cggcggaaac    1080
gaccccgcga accgcgaagc aacctggctc tcgggctacc cgaccgacag cgagctgtac    1140
aagttaattg cctccgcgaa cgcaatccgg aactatgcca ttagcaaaga tacaggattc    1200
```

| | |
|---|---:|
| gtgacctaca agaactggcc catctacaaa gacgacacaa cgatcgccat gcgcaagggc | 1260 |
| acagatgggt cgcagatcgt gactatcttg tccaacaagg gtgcttcggg tgattcgtat | 1320 |
| accctctcct tgagtggtgc gggttacaca gccggccagc aattgacgga ggtcattggc | 1380 |
| tgcacgaccg tgacggttgg ttcggatgga aatgtgcctg ttcctatggc aggtgggcta | 1440 |
| cctagggtat tgtatccgac tgagaagttg gcaggtagca agatctgtag tagctcgtga | 1500 |

<210> SEQ ID NO 2
<211> LENGTH: 1923
<212> TYPE: DNA
<213> ORGANISM: Aspergillus niger

<400> SEQUENCE: 2

| | |
|---|---:|
| atgtcgttcc gatctctact cgccctgagc ggcctcgtct gcacagggtt ggcaaatgtg | 60 |
| atttccaagc gcgcgacctt ggattcatgg ttgagcaacg aagcgaccgt ggctcgtact | 120 |
| gccatcctga ataacatcgg ggcggacggt gcttgggtgt cgggcgcgga ctctggcatt | 180 |
| gtcgttgcta gtcccagcac ggataacccg gactacttct acacctggac tcgcgactct | 240 |
| ggtctcgtcc tcaagaccct cgtcgatctc ttccgaaatg gagataccag tctcctctcc | 300 |
| accattgaga actacatctc cgcccaggca attgtccagg gtatcagtaa cccctctggt | 360 |
| gatctgtcca gcggcgctgg tctcggtgaa cccaagttca atgtcgatga gactgcctac | 420 |
| actggttctt ggggacggcc gcagcagat ggtccggctc tgagagcaac tgctatgatc | 480 |
| ggcttcgggc agtggctgct tgacaatggc tacaccagca ccgcaacgga cattgtttgg | 540 |
| cccctcgtta ggaacgacct gtcgtatgtg gctcaatact ggaaccagac aggatatgat | 600 |
| ctctgggaag aagtcaatgg ctcgtctttc tttacgattg ctgtgcaaca ccgcgccctt | 660 |
| gtcgaaggta gtgccttcgc gacggccgtc ggctcgtcct gctcctggtg tgattctcag | 720 |
| gcacccgaaa ttctctgcta cctgcagtcc ttctggaccg gcagcttcat tctggccaac | 780 |
| ttcgatagca gccgttccgg caaggacgca aacacccctcc tgggaagcat ccacaccttt | 840 |
| gatcctgagg ccgcatgcga cgactccacc ttccagccct gctccccgcg cgcgctcgcc | 900 |
| aaccacaagg aggttgtaga ctcttttccgc tcaatctata ccctcaacga tggtctcagt | 960 |
| gacagcgagg ctgttgcggt gggtcggtac cctgaggaca cgtactacaa cggcaacccg | 1020 |
| tggttcctgt gcaccttggc tgccgcagag cagttgtacg atgctctata ccagtgggac | 1080 |
| aagcagggt cgttggaggt cacagatgtg tcgctggact tcttcaaggc actgtacagc | 1140 |
| gatgctgcta ctggcaccta ctcttcgtcc agttcgactt atagtagcat tgtagatgcc | 1200 |
| gtgaagactt tcgccgatgg cttcgtctct attgtggaaa ctcacgccgc aagcaacggc | 1260 |
| tccatgtccg agcaatacga caagtctgat ggcgagcagc tttccgctcg cgacctgacc | 1320 |
| tggtcttatg ctgctctgct gaccgccaac aaccgtcgta actccgtcgt gcctgcttct | 1380 |
| tggggcgaga cctctgccag cagcgtgccc ggcacctgtg cggccacatc tgccattggt | 1440 |
| acctacagca gtgtgactgt cacctcgtgg ccgagtatcg tggctactgg cggcaccact | 1500 |
| acgacggcta cccccactgg atccggcagc gtgacctcga ccagcaagac caccgcgact | 1560 |
| gctagtaaga ccagcaccag tacgtcatca acctcctgta ccactcccac cgccgtggct | 1620 |
| gtgactttcg atctgacagc taccaccacc tacggcgaga acatctacct ggtcggatcg | 1680 |
| atctctcagc tgggtgactg ggaaaccagc gacggcatag ctctgagtgc tgacaagtac | 1740 |
| acttccagcg acccgctctg gtatgtcact gtgactctgc cggctggtga gtcgtttgag | 1800 |
| tacaagttta tccgcattga gagcgatgac tccgtggagt gggagagtga tcccaaccga | 1860 |

```
gaatacaccg ttcctcaggc gtgtggaacg tcgaccgcga cggtgactga cacctggcgg    1920
tag                                                                  1923

<210> SEQ ID NO 3
<211> LENGTH: 1185
<212> TYPE: DNA
<213> ORGANISM: Aspergillus niger

<400> SEQUENCE: 3
atggtcgtct tcagcaaaac cgctgccctc gttctgggtc tgtcctccgc cgtctctgcg      60
gcgccggctc ctactcgcaa gggcttcacc atcaaccaga ttgcccggcc tgccaacaag     120
acccgcacca tcaacctgcc aggcatgtac gcccgttccc tggccaagtt tggcggtacg     180
gtgccccaga gcgtgaagga ggctgccagc aagggtagtg ccgtgaccac gccccagaac     240
aatgacgagg agtacctgac tcccgtcact gtcggaaagt ccaccctcca tctggacttt     300
gacaccggat ctgcagatct ctgggtcttc tcggacgagc tcccttcctc ggagcagacc     360
ggtcacgatc tgtacacgcc tagctccagc gcgaccaagc tgagcggcta cacttgggac     420
atctcctacg gtgacggcag ctcggccagt ggagacgtgt accgggatac tgtcactgtc     480
ggcggtgtca ccaccaacaa gcaggctgtt gaagcagcca gcaagatcag ctccgagttc     540
gttcaggaca cggccaatga cggccttctg ggactggcct ttagctccat taacactgtc     600
cagcccaagg cgcagaccac cttcttcgac accgtcaagt cccagctgga ctctccccgtt    660 ttcgccgtgc agctgaagca cgacgccccc ggtgtttacg actttggcta catcgatgac     720
tccaagtaca ccggttctat cacctacacg gatgccgata gctcccaggg ctactggggc     780
ttcagcaccg acggctacag tatcggtgac ggcagctcta gctccagcgg cttcagcgcc     840
attgctgaca ccggtaccac cctcatcctc ctcgatgacg aaatcgtctc cgcctactac     900
gagcaggttt ctggcgctca ggagagcgag gaagccggtg gctacgtttt ctcttgctcg     960
accaaccccc ctgacttcac tgtcgtgatt ggcgactaca aggccgtcgt tccgggcaag    1020
tacatcaact acgctcccat ctcgactggc agctccacct gctttggcgg tatccagagc    1080
aacagcggtc tgggactgtc catcctgggc gatgtgttct tgaagagcca gtacgtggtc    1140
ttcaactctg agggtcctaa gctgggattc gccgctcagg cttag                    1185

<210> SEQ ID NO 4
<211> LENGTH: 30
<212> TYPE: DNA
<213> ORGANISM: Aspergillus oryzae

<400> SEQUENCE: 4
ggatccatga tggtcgcgtg gtggtctgta                                        30

<210> SEQ ID NO 5
<211> LENGTH: 30
<212> TYPE: DNA
<213> ORGANISM: Aspergillus oryzae

<400> SEQUENCE: 5
actagttcac gagctactac agatcttgct                                        30

<210> SEQ ID NO 6
<211> LENGTH: 27
<212> TYPE: DNA
<213> ORGANISM: Aspergillus niger
```

```
<400> SEQUENCE: 6
ggatccatgt cgttccgatc tctactc                                             27

<210> SEQ ID NO 7
<211> LENGTH: 24
<212> TYPE: DNA
<213> ORGANISM: Aspergillus niger

<400> SEQUENCE: 7
actagtctac cgccaggtgt cagt                                                24

<210> SEQ ID NO 8
<211> LENGTH: 27
<212> TYPE: DNA
<213> ORGANISM: Aspergillus niger

<400> SEQUENCE: 8
ggatccatgg tcgtcttcag caaaacc                                             27

<210> SEQ ID NO 9
<211> LENGTH: 26
<212> TYPE: DNA
<213> ORGANISM: Aspergillus niger

<400> SEQUENCE: 9
actagtctaa gcctgagcgg cgaatc                                              26
```

GENETICALLY RECOMBINANT SACCHAROMYCES CEREVISIAE FOR DEGRADING KITCHEN WASTE

FIELD OF THE INVENTION

The present invention is related to fields of genetic engineering and fermentation engineering, and in particular, to a genetically recombinant *Saccharomyces cerevisiae* useful for degrading and utilizing kitchen waste.

BACKGROUND

Fuel ethanol for motor vehicles is substantially generated using grain and corns at present in China. Large-scale production of fuel ethanol will results in competitive usage of foods, leading to rising food prices and potential food shortage. A possible solution uses non-food renewable biomass to generate ethanol. Kitchen waste comprises a huge amount of renewable biomass. Over 60 million tons of kitchen waste is produced every year in China, and most are used to feed livestock, or delivered to landfill or incineration, resulting in severe environmental pollution. Only a small part is utilized to for example make compost or biogas, but with low economic interest. Therefore, it is promising to use kitchen waste to produce fuel ethanol, which both converts wastes to valuables and relieves food and energy shortage crisis.

Kitchen waste is a nutrition-enriched renewable biomass containing over 95% organics such as starch, saccharides, proteins, lipids, vitamins and elements such as N, P, S, K, Ca, and Mg. This enables kitchen waste to be biologically reusable. However, high contents of water and nutrition in the kitchen waste make microorganisms propagate rapidly at room temperature, taking advantage of the organics and mineral salts, causing the waste to decay and stink which brings challenges to process.

*Saccharomyces cerevisiae* is industrially preferable strain for ethanol fermentation which is capable of efficiently convert glucose to ethanol. However, the strain can not naturally use the starch and proteins contained in kitchen waste as carbon and nitrogen sources to generate ethanol due to lack of enzymes for degrading starch to glucose and enzymes for degrading proteins to polypeptides and amino acids.

It is therefore necessary to introduce genes encoding enzymes degrading starch and proteins to the *Saccharomyces cerevisiae* so that the strain will be able to take advantage of the self-expressing amylase and protease to convert the starch and proteins in kitchen waste to carbon and nitrogen sources, such that the waste can be converted to fuel ethanol for industrial purpose.

SUMMARY

One aspect of the invention provides a genetically recombinant *Saccharomyces cerevisiae* useful for degrading and utilizing kitchen wastes.

Another aspect of the invention provides a construction method for a genetically recombinant *Saccharomyces cerevisiae* useful for degrading and utilizing kitchen wastes.

The genetically recombinant *Saccharomyces cerevisiae* useful for degrading and utilizing kitchen wastes is constructed by introducing α-amylase (AMY) gene, glucoamylase (GA) gene and acid protease (AP) gene into *Saccharomyces cerevisiae* through a *Saccharomyces cerevisiae* expression vector and achieving correct expression and secretion.

The present invention relies on the introduction and expression of AMY, GA and AP genes. A *Saccharomyces cerevisiae* expression vector is used as a tool. Preferably, the *Saccharomyces cerevisiae* expression vector is a *Saccharomyces cerevisiae* multi-gene co-expression vector which enables co-transduction of AMY, GA and AP genes into *Saccharomyces cerevisiae*. Preferably, the *Saccharomyces cerevisiae* multi-gene co-expression vector is pScIKP, the preparation of which was disclosed in Chinese Patent No. ZL 200810029630.6. Other types of *Saccharomyces cerevisiae* multi-gene co-expression vector can also be used.

A method for constructing a genetically recombinant *Saccharomyces cerevisiae* useful for degrading and utilizing kitchen wastes is provided, which comprising S1. obtaining gene sequences encoding α-amylase, glucoamylase and acid protease respectively by using PCR amplification; introducing an artificial mutation to mutate the residue C at position 1566 to T for the gene encoding glucoamylase, and the residue C at position 1155 to T for the gene encoding acid protease;

S2. introducing the genes encoding α-amylase, glucoamylase and acid protease into a *Saccharomyces cerevisiae* expression vector to obtain a multi-gene co-expression vector;

S3. linearizing the multi-gene co-expression vector by a restriction endonuclease, and transform to a *Saccharomyces cerevisiae* to obtain a recombinant *Saccharomyces cerevisiae*.

In a preferable embodiment, step S2 comprises steps of

S11. digesting the *Saccharomyces cerevisiae* expression vector, the α-amylase gene, the glucoamylase gene, and the acid protease gene by restriction endonucleases;

S12. ligating the α-amylase gene, the glucoamylase gene, and the acid protease gene into the *Saccharomyces cerevisiae* expression vector to obtain three recombinant single-gene vectors;

S13. cutting from the three recombinant single-gene vectors to obtain a complete α-amylase gene expression cassette, a glucoamylase gene expression cassette, and an acid protease gene expression cassette, respectively, by restriction endonucleases, with each gene expression cassette containing its own promoter and terminator fragments, and introducing the gene expression cassettes into one *Saccharomyces cerevisiae* expression vector in series in the form of cassettes amy-ga-ap.

Preferably, the restriction endonuclease used in step S3 is ApaI.

Preferably, the transform step in step S3 is performed by electrotransformation, freezing, or chemical reagents.

Preferably, the restriction endonucleases used in step S11 are BamHI and SpeI; and the restriction endonucleases used in step S13 are isocaudarners NheI and XbaI.

Preferably, the α-amylase gene is the α-amylase gene originated from *Aspergillus oryzae*; the glucoamylase gene is the glucoamylase gene originated from *Aspergillus niger*; and the acid protease gene is the acid protease gene originated from *Aspergillus niger*.

In a most preferable embodiment, the α-amylase gene is the α-amylase gene originated from *Aspergillus oryzae* CICC 40344 purchased from China Center of Industrial Culture Collection, CICC); the glucoamylase gene is the glucoamylase gene originated from *Aspergillus niger* CICC 40179 purchased from China Center of Industrial Culture Collection, CICC); and the acid protease gene is the acid protease gene originated from *Aspergillus niger* CICC 40179.

The nucleic acid sequence of the α-amylase gene originated from *Aspergillus oryzae* CICC 40344 is shown in SEQ ID NO. 1, the nucleic acid sequence of the glucoamylase gene originated from *Aspergillus niger* CICC 40179 is shown in SEQ ID NO. 2 with the nucleotide residue C (cytimidine) at position 1566 artificially mutated to T (thymine), and the nucleic acid sequence of the acid protease gene originated from *Aspergillus niger* CICC 40179 is shown in SEQ ID NO. 3 with the nucleotide residue C (cytimidine) at position 1155 artificially mutated to T (thymine).

The present invention is advantageous over conventional technologies.

*Saccharomyces cerevisiae* is not able to utilize the starch or proteins enriched in kitchen wastes as carbon or nitrogen sources to generate ethanol when it is not fermented. To enable the *Saccharomyces cerevisiae* to utilize kitchen wastes as raw materials to ferment ethanol, genes encoding enzymes for degrading starch and proteins are introduced into *Saccharomyces cerevisiae* and expressed, such that the *Saccharomyces cerevisiae* so obtained are capable of secreting amylases and protease to degrade the starch and proteins in kitchen wastes to produce carbon and nitrogen sources such as glucose, polypeptides and amino acids for ethanol fermentation.

The key point in the invention is to successfully introduce genes encoding α-amylase, glucoamylase and acid protease into a *Saccharomyces cerevisiae* through a *Saccharomyces cerevisiae* multi-gene co-expression vector and make the genes expressed. To this end, a recombinant vector carrying amy, ga, ap gene cassettes needs to be constructed firstly. It is required that the gene sequences can not harbor restriction sites for isocaudarners NheI and XbaI, because otherwise the gene sequences would be broken during the cassettes were cut from the single-expression vectors, resulting in incomplete introduction into the co-expression vector. For this purpose, the nucleotide residue C at position 1566 in the glucoamylase gene is mutated to T, causing the disruption of a restriction site of NheI, and the nucleotide residue C at position 1155 in the acid protease gene is mutated to T, causing the disruption of a restriction site of XbaI, without alternation to the amino acid sequences of the proteins encoded by these genes. A recombinant co-expression vector pScIKP-amy-ga-ap carrying three complete gene expression cassettes are obtained.

DETAILED DESCRIPTION OF THE INVENTION

Figure 1:
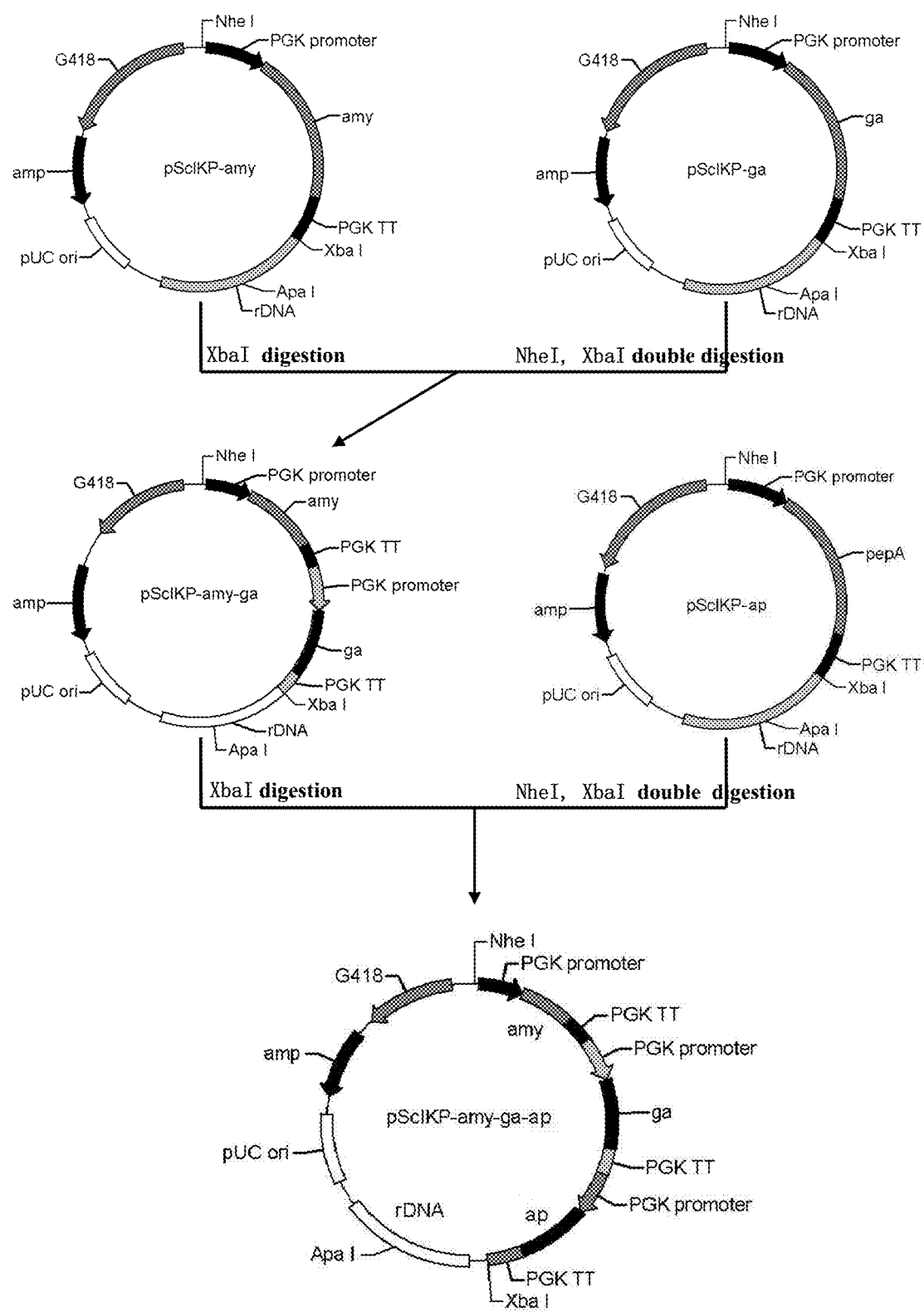
FIG. 1 is a flow chart showing construction of a recombinant *Saccharomyces cerevisiae* multi-gene expression vector pScIKP-amy-ga-ap.

The present invention will now be further illustrated with specific examples and accompany drawings which should not be constructed as limiting to the scope of the invention.

The yeast *Saccharomyces cerevisiae* AS2.489 is purchased from Microbiological Culture Collection Center, Institute of Microbiology, Chinese Academy of Sciences. The vector pScIKP is constructed and preserved by the Research Centre for Molecular Biology of Jinan University, the construction method of which can be found in Chinese Patent No. ZL 200810029630.6.

Example 1 Cloning of α-Amylase Gene Amy, Glucoamylase Gene Ga and Acid Protease Gene Ap Primers were designed based on the sequences available from GenBank for the gene amy of *Aspergillus oryzae* [Accession number XM_001821384], the gene ga of *Aspergillus niger* [Accession number XM_001390493.1], and the gene ap of *Aspergillus niger* [Accession number XM_001401056.2]. Appropriate restriction sites were introduced into the primers:

Primers for Amy Gene Amplification:

```
                                         (SEQ ID NO: 4)
Forward: 5'-GGATCCATGATGGTCGCGTGGTGGTCTGTA-3'
               ↑
               |
             BamH I
                                         (SEQ ID NO: 5)
Reverse: 5'-ACTAGTTCACGAGCTACTACAGATCTTGCT-3'
               ↑
               |
             Spe I
```

Primers for Ga Gene Amplification:

```
                                         (SEQ ID NO: 4)
Forward: 5'-GGATCCATGTCGTTCCGATCTCTACTC-3'
               ↑
               |
             BamH I
                                         (SEQ ID NO: 5)
Reverse: 5'-ACTAGTCTACCGCCAGGTGTCAGT-3'
               ↑
               |
             Spe I
```

Primers for Ap Gene Amplification:

(SEQ ID NO: 8)
Forward: 5'-GGATCCATGGTCGTCTTCAGCAAAACC-3'
          BamH I (SEQ ID NO: 9)
Reverse: 5'-ACTAGTCTAAGCCTGAGCGGCGAATC-3'
          Spe I The total RNA was extracted from *Aspergillus oryzae* CICC 40344 and the target gene was amplified by RT-PCR. The RT-PCR amplified products were ligated into a pGEM-T Easy vector (Promega) and verified by sequencing.

PCR reaction conditions for the amy gene were set as follows.

| 94° C. | 5 min |  |
|---|---|---|
| 94° C. | 30 s |  |
| 53.3° C. | 30 s | 30 cycles |
| 72° C. | 100 s |  |
| 72° C. | 10 min |  |

The total RNA was extracted from *Aspergillus niger* CICC 40179 and the target gene was amplified by RT-PCR. The RT-PCR amplified products of genes ga and ap were ligated into a pGEM-T Easy vector (Promega), respectively, and verified by sequencing.

PCR reaction conditions for the ga gene were set as follows.

| 94° C. | 5 min |  |
|---|---|---|
| 94° C. | 30 s |  |
| 57° C. | 30 s | 30 cycles |
| 72° C. | 100 s |  |
| 72° C. | 10 min |  |

PCR reaction conditions for the ap gene were set as follows.

| 94° C. | 5 min |  |
|---|---|---|
| 94° C. | 30 s |  |
| 58° C. | 30 s | 30 cycles |
| 72° C. | 100 s |  |
| 72° C. | 10 min |  |

The nucleic acid sequence of the α-amylase gene amy originated from *Aspergillus oryzae* CICC 40344 is shown in SEQ ID NO. 1, the nucleic acid sequence of the glucoamylase gene ga originated from *Aspergillus niger* CICC 40179 is shown in SEQ ID NO. 2 with the nucleotide residue C (cytimidine) at position 1566 artificially mutated to T (thymine), and the nucleic acid sequence of the acid protease gene ap originated from *Aspergillus niger* CICC 40179 is shown in SEQ ID NO. 3 with the nucleotide residue C (cytimidine) at position 1155 artificially mutated to T (thymine).

Example 2 Construction of the Co-Expression Vector Carrying Genes Encoding the Three Enzymes The process of construction is shown in FIG. 1.

The amy, ga and ap coding sequences obtained from Example 1 were double digested from pGEM-T Easy vectors using BamHI and SpeI, and then ligated into the vector pScIKP previously digested by the same restriction endonucleases, to obtain recombinant plasmids pScIKP-amy, pScIKP-ga and pScIKP-ap.

pScIKP-ga was double digested by NheI and XbaI to obtain the ga gene expression cassette containing the PGK promoter and the PGK terminator from *S. cerevisiae*. NheI single digestion of pScIKP-amy results in linearization. T4 DNA ligase was used to ligate the ga cassette and the linearized pScIKP-amy, taking advantage of the fact that NheI and XbaI are isocaudarners, to give a recombinant plasmid pScIKP-amy-ga. Similarly, pScIKP-ap was double digested by NheI and Xba I to obtain the ap gene expression cassette containing the PGK promoter and the PGK terminator from *S. cerevisiae*, which is then ligated with the linearized pScIKP-amy-ga digested by NheI to give a recombinant plasmid pScIKP-amy-ga-ap.

Example 3 Screening and Validation of Recombinant Yeast Transformants

Resistance tolerance was performed for *Saccharomyces cerevisiae* AS2.489 over resistance selection markers G418 prior to electrotransformation. It was found that the yeast can not grow on an YPD plate containing G418 of 150 µg/nil, so concentrations above 150 µg/ml G418 can be used for recombinant screening.

Figure 2:
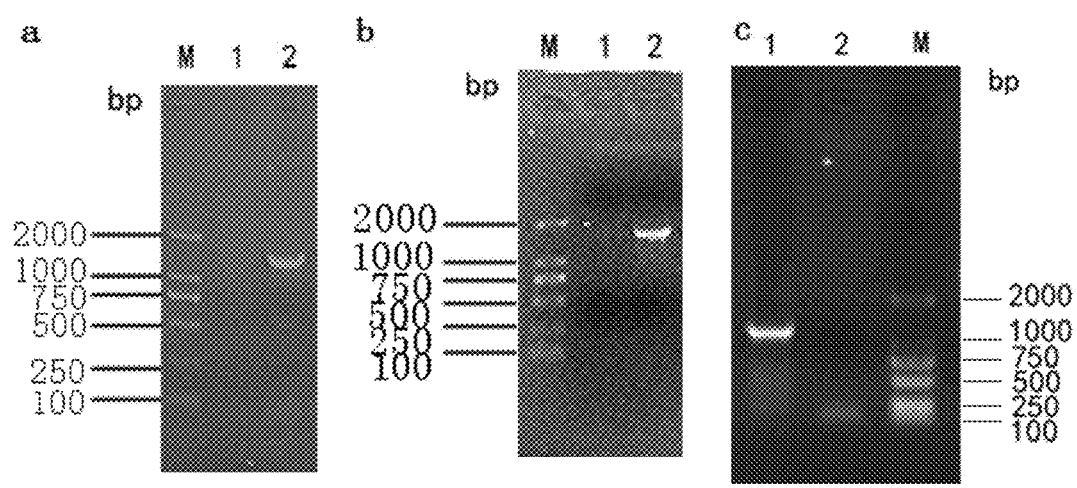
FIG. 2 shows the PCR results of positive transformants, (a) amplified fragments for α-amylase, (b) amplified fragments for glucoamylase and (c) amplified fragments for acid protease.

The recombinant plasmid pScIKP-amy-ga-ap obtained from Example 2 was linearized by ApaI and introduced into *Saccharomyces cerevisiae* AS2.489 by electrotransformation. The yeast was cultured on an YPD agar plate for 3-4 days in the presence of G418 at 200 µg/ml. The colony normally grown was selected for screening for the positive transformant by PCR using specific primers for each of the genes. The positive PCR results (FIG. 2), demonstrated that the genes were incorporated into the genome of the *Saccharomyces cerevisiae*.

Example 4 Enzyme Activity Assay for the Amylases and Protease Secreted by the Recombinant *Saccharomyces cerevisiae*

Figure 3:
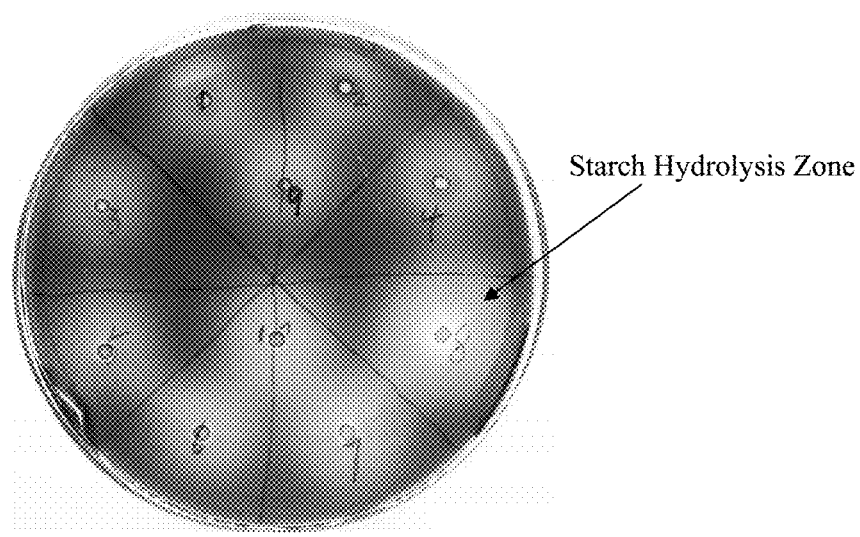
FIG. 3: Enzyme activity assay for α-amylase and glucoamylase of the recombinant yeast by iodine staining.

The positive transformant obtained from Example 3 was inoculated on an YNBS plate (YNB 6.7 g/l, soluble starch 10 g/l, and agar powder 15 g/l) containing 1% soluble starch, and cultured in an incubator at 30° C. for 72 h. The plate was stained by iodine vapor. The results were shown in FIG. 3, where obvious transparent zones formed because of the hydrolysis of starch were observed around the colony, indicating that the transformant can utilize the starch in the plate as carbon source to grow.

Figure 4:
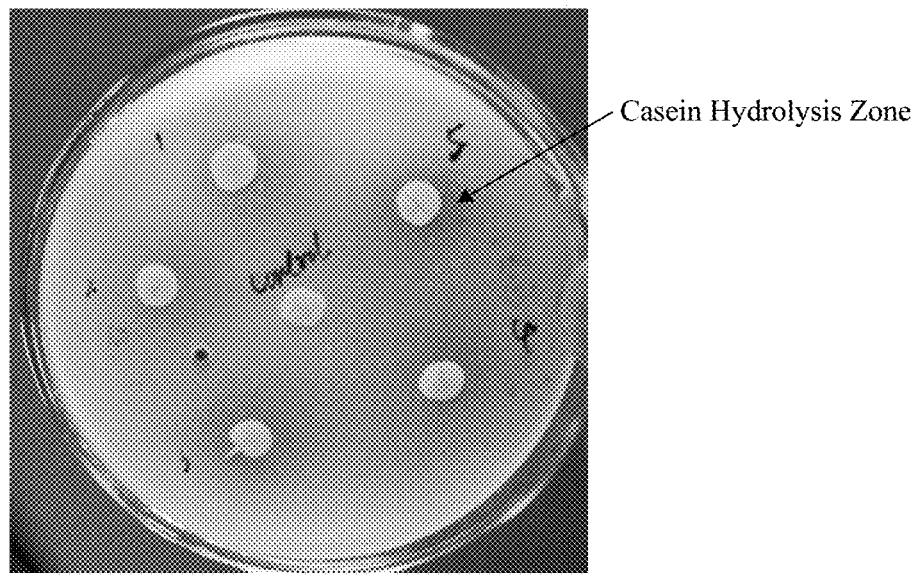
FIG. 4: Enzyme activity assay for acid protease of the recombinant yeast by casein developing process.

The positive transformant obtained from Example 3 was inoculated in a solid YPD medium (0.5 g yeast extract, 2 g peptone, agar 1.5 g, added to 100 ml using 1% casein solution) containing 1% casein and incubated at 30° C. for 3-4 days. As shown in FIG. 4, the casein was degraded by protease and thus obvious transparent zones formed by casein hydrolysis were observed around the colony.

Example 5 Ethanol Production by Fermentation of Kitchen Waste Using the Recombinant Yeast (1) Medium Composition The seeding medium: YPD medium (yeast extract 10 g/l, tryptone 20 g/l, glucose 20 g/l), subject to autoclaved sterilization.

Fermentation medium: kitchen wastes collected from food residues from a canteen in a university in Guangzhou. Non-food residues were removed and the kitchen wastes were crushed by a crushing processor dedicated for garbage treatment. The wastes were mixed thoroughly and loaded to 1 L conical flasks and sterilized at 121° C. for 20 min for fermentation by the recombinant yeast. The composition of the kitchen waste mixture was determined as the following: water 73.8%, dry matter 26.2% (including starch 9.7%, protein 1.0%, soluble saccharides 4.4%, others 11.1%), pH 6.1.

(2) Fermentation

The recombinant *Saccharomyces cerevisiae* was activated before inoculated to a 25 ml YPD seeding yeast medium at 2% inoculation. The yeast was cultured in an air shaker incubator at 30° C., 200 rpm for 24 h and then inoculated to a 200 ml YPD medium at 10% inoculation for an enlarged culture at 30° C., 250 rpm until the logarithmic phase. When cell reaches about $0.8$~$1.2 \times 10^8$/mL, about 20% budding rate and no more than 1% mortality, it indicated that seeding yeast was mature.

The culture was transferred to the sterilized conical flasks containing the kitchen wastes at a volume of 10% of the fermentation medium and started fermentation.

Figure 5:
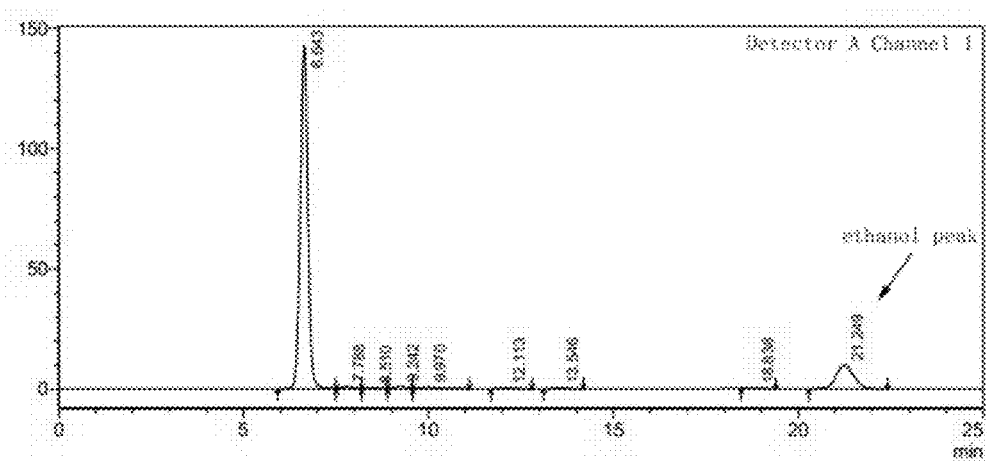
FIG. 5: HPLC results detecting ethanol levels in the fermentation broth by the present recombinant yeast.

The fermentation conditions were set as follows: 30° C., 250 rpm, natural pH, aerated fermentation for 4 h; then 30° C., 150 rpm, natural pH, and anaerobic fermentation for 60 h. Sampling was performed every 12 h during fermentation, and the production of ethanol was detected by HPLC (FIG. 5). It was shown that the maximum ethanol production was achieved at 52 h, reaching a concentration of 66 g/L. The conversion rate of kitchen waste-ethanol reached up to 1 g ethanol per 4 g kitchen wastes (dry weight).

The results showed that the recombinant *Saccharomyces cerevisiae* as constructed by the present invention was able to degrade and utilize kitchen wastes and converted them to ethanol. The recombinant yeast was therefore named by the inventors as "Waste-swallow Yeast 1".

The invention claimed is:

1. A genetically recombinant *Saccharomyces cerevisiae* useful for degrading and utilizing kitchen wastes, comprising genes encoding α-amylase (AMY), glucoamylase (GA) and acid protease (AP), wherein the genetically recombinant *Saccharomyces cerevisiae* is configured to be able to convert kitchen wastes to ethanol with a conversion rate up to 1 g ethanol per 4 g dry kitchen wastes.

2. The genetically recombinant *Saccharomyces cerevisiae* useful for degrading and utilizing kitchen wastes of claim 1, wherein the genes are introduced into *Saccharomyces cerevisiae* through a *Saccharomyces cerevisiae* multi-gene co-expression vector, wherein the *Saccharomyces cerevisiae* multi-gene co-expression vector is vector pScIKP.

3. A method for constructing the genetically recombinant *Saccharomyces cerevisiae* useful for degrading and utilizing kitchen wastes of claim 1, wherein the method comprises steps of A. obtaining gene sequences encoding α-amylase, glucoamylase and acid protease respectively by using PCR amplification; introducing an artificial mutation to mutate nucleotide residue C at position 1566 to T for the gene encoding glucoamylase, and nucleotide residue C at position 1155 to T for the gene encoding acid protease;

B. introducing the genes encoding α-amylase, glucoamylase and acid protease into a *Saccharomyces cerevisiae* expression vector to obtain a multi-gene co-expression vector;

C. linearizing the multi-gene co-expression vector by a restriction endonuclease, and transform the linearized vector to a *Saccharomyces cerevisiae* to obtain the genetically recombinant *Saccharomyces cerevisiae*.

4. The method of claim 3, wherein step B comprises steps of

D. digesting the *Saccharomyces cerevisiae* expression vector, the α-amylase gene, the glucoamylase gene, and the acid protease gene, by restriction endonucleases;

E. ligating the genes encoding α-amylase, glucoamylase, and acid protease respectively into the *Saccharomyces cerevisiae* expression vector to obtain three recombinant single-gene expression vectors;

F. cutting from the three recombinant single-gene vectors to obtain a complete α-amylase gene expression cassette, a glucoamylase gene expression cassette, and an acid protease gene expression cassette, respectively, by restriction endonucleases, with each gene expression cassette containing its own promoter and terminator fragments, and introducing the gene expression cassettes into one *Saccharomyces cerevisiae* expression vector in series in the form of cassettes amy-ga-ap.

5. The method of claim 3, wherein the restriction endonuclease used in step C is ApaI.

6. The method of claim 3, wherein the transform step in step C is performed by electrotransformation, freezing, or chemical reagents.

7. The method of claim 4, wherein the restriction endonucleases used in step D are BamHI and SpeI; and the restriction endonucleases used in step F are isocaudomers NheI and XbaI.

8. The method of claim 3, wherein the gene encoding α-amylase is the α-amylase gene originated from *Aspergillus oryzae*; the gene encoding glucoamylase gene is the glucoamylase gene originated from *Aspergillus niger*; and the gene encoding acid protease gene is the acid protease gene originated from *Aspergillus niger*.

9. The method of claim 4, wherein the gene encoding α-amylase is the α-amylase gene originated from *Aspergil-*

*lus oryzae*; the gene encoding glucoamylase gene is the glucoamylase gene originated from *Aspergillus niger*; and the gene encoding acid protease gene is the acid protease gene originated from *Aspergillus niger*.

10. The method of claim 7, wherein the gene encoding α-amylase is the α-amylase gene originated from *Aspergillus oryzae*; the gene encoding glucoamylase gene is the glucoamylase gene originated from *Aspergillus niger*; and the gene encoding acid protease gene is the acid protease gene originated from *Aspergillus niger*.

* * * * *